(12) United States Patent
Lu (10) Patent No.: US 9,476,603 B2
(45) Date of Patent: Oct. 25, 2016

(54) HEATER WITH HUMIDIFYING DEVICE

(71) Applicant: Dong GUAN SONG WEI ELECTRIC TECHNOLOGY CO., LTD., Dongguan (CN)

(72) Inventor: Weilin Lu, Dongguan (CN)

(73) Assignee: DONG GUAN SONG WEI ELECTRIC TECHNOLOGY CO., LTD, Dongguan, Guangdong (CN)

( * ) Notice: Subject to any disclaimer, the term of this patent is extended or adjusted under 35 U.S.C. 154(b) by 28 days.

(21) Appl. No.: 14/569,580

(22) Filed: Dec. 12, 2014

(65) Prior Publication Data

US 2016/0169541 A1  Jun. 16, 2016

(51) Int. Cl.
| | |
|---|---|
| *F24F 6/00* | (2006.01) |
| *A61L 9/22* | (2006.01) |
| *A61L 9/12* | (2006.01) |
| *F24F 6/04* | (2006.01) |
| *F24F 6/12* | (2006.01) |

(52) U.S. Cl.
CPC .. *F24F 6/00* (2013.01); *A61L 9/12* (2013.01); *A61L 9/22* (2013.01); *F24F 6/043* (2013.01); *F24F 6/12* (2013.01); *F24F 2006/006* (2013.01); *F24F 2006/008* (2013.01)

(58) Field of Classification Search
CPC .............. F24F 6/043; F24F 6/12; F24F 6/00; F24F 2006/006; F24F 2006/008; A61L 9/12; A61L 9/22
See application file for complete search history.

(56) References Cited

U.S. PATENT DOCUMENTS

| | | | | |
|---|---|---|---|---|
| 2,335,056 A * | 11/1943 | Grison | ....................... | A61L 9/20 15/246.2 |
| 3,628,312 A * | 12/1971 | Stoop | ........................ | F24F 6/06 261/92 |
| 6,053,482 A * | 4/2000 | Glenn | ..................... | F24F 6/043 261/104 |
| 6,293,474 B1 * | 9/2001 | Helf | ...................... | A01M 1/205 239/102.1 |
| 6,390,378 B1 * | 5/2002 | Briscoe, Jr. | ........... | A23L 3/3418 236/44 C |
| 6,446,880 B1 * | 9/2002 | Schram | ............... | B05B 17/0684 222/570 |
| 6,581,917 B2 * | 6/2003 | Mulvaney | ............... | F24F 6/043 261/107 |
| 6,622,993 B2 * | 9/2003 | Mulvaney | ............... | G01F 23/22 261/107 |
| 6,736,133 B2 * | 5/2004 | Bachinski | ............... | F24B 1/185 126/507 |

(Continued)

FOREIGN PATENT DOCUMENTS

| | | | | | |
|---|---|---|---|---|---|
| AU | WO 2015135040 A1 * | 9/2015 | .......... | A61M 16/109 |
| DE | 2839041 A1 * | 3/1980 | ................ | F24F 1/00 |

(Continued)

*Primary Examiner* — Duane Smith
*Assistant Examiner* — Stephen Hobson (57) ABSTRACT

The present invention discloses a heater with a humidifying device. The humidifying device includes a water container, a cotton rod, a fixing knob, an atomization plate, a hollow pipe, and a fog output box. Through the cotton rod, water is sent to the atomization plate to directly generate atomized particles. The heater is combined with an air purifying device, the humidifying device, and a heating device to provide multiple functions. An air outlet outputs warm wind, humidified air and purified air, so the user can feel fresh but not dry warm wind.

9 Claims, 8 Drawing Sheets

(56) References Cited

U.S. PATENT DOCUMENTS

| | | | | |
|---|---|---|---|---|
| 6,793,205 | B2* | 9/2004 | Eom | F24F 6/12 261/142 |
| 7,934,702 | B1* | 5/2011 | Feldstein | F24F 6/14 126/113 |
| 8,296,993 | B2* | 10/2012 | Modlin | A01M 1/205 239/102.2 |
| 8,625,252 | B2* | 1/2014 | Kitagaito | A61L 9/22 361/230 |
| 8,720,439 | B1* | 5/2014 | Kolkowski | A61M 16/16 128/203.12 |
| 2005/0212152 | A1* | 9/2005 | Reens | F24F 6/12 261/81 |
| 2006/0110141 | A1* | 5/2006 | Burkett | F24H 3/0405 392/375 |
| 2006/0130492 | A1* | 6/2006 | Park | A47J 36/2433 62/3.6 |
| 2009/0096118 | A1* | 4/2009 | Brown | F24F 6/04 261/128 |
| 2010/0254686 | A1* | 10/2010 | Tyburk | F24H 3/0417 392/373 |
| 2011/0162528 | A1* | 7/2011 | Yamaguchi | A01N 3/00 96/251 |
| 2011/0226868 | A1* | 9/2011 | Modlin | A01M 1/205 239/102.1 |
| 2011/0233289 | A1* | 9/2011 | Bortoletto | F25D 17/042 236/44 A |
| 2012/0111970 | A1* | 5/2012 | Hogan | B05B 17/0646 239/102.2 |
| 2012/0112371 | A1* | 5/2012 | Kanel | F24F 6/02 261/28 |
| 2012/0222548 | A1* | 9/2012 | Lev | F24F 6/12 95/1 |
| 2012/0308214 | A1* | 12/2012 | Tyburk | F24F 13/20 392/407 |
| 2013/0154134 | A1* | 6/2013 | Lev | F24F 6/12 261/141 |
| 2013/0255664 | A1* | 10/2013 | Dresner | F24H 8/006 126/508 |
| 2013/0334716 | A1* | 12/2013 | Ching | F24F 6/12 261/81 |
| 2014/0232022 | A1* | 8/2014 | Chung | B05B 15/065 261/78.1 |
| 2015/0241072 | A1* | 8/2015 | Kim | F24F 11/02 236/44 C |
| 2016/0067369 | A1* | 3/2016 | Muhammad | A61L 9/22 422/109 |
| 2016/0131372 | A1* | 5/2016 | Choi | F24F 3/14 62/189 |
| 2016/0169537 | A1* | 6/2016 | Lu | F24D 13/00 422/123 |

FOREIGN PATENT DOCUMENTS

| | | | | |
|---|---|---|---|---|
| JP | WO 2013146639 | A1 * | 10/2013 | B05B 15/06 |
| NL | WO 2014001952 | A1 * | 1/2014 | F24F 6/043 |

* cited by examiner

HEATER WITH HUMIDIFYING DEVICE

BACKGROUND OF THE INVENTION

1. Field of the Invention

The present invention relates to a heater, and more particularly to a heater with a humidifying device.

2. Description of the Prior Art

A heater becomes an essential appliance. The existing heater only has a single function, providing warm air. But, because the current environmental pollution is getting worse, people pay more attention to health. Humidity has a very close relationship with people's lives. When the humidity is too little, people's skin is dry, rough, and aging. Sometimes, the lips are also dry or the throat is itching, etc. Therefore, a heater having a humidifying function has been developed, as disclosed in Chinese Utility Model Reg. No. 200620085317.0 titled "HEATER HAVING HUMIDIFYING DEVICE". The heater has a water container. The water container is provided with an electric heating tube therein. The side of the water container is provided with a temperature control box. The electric heating tube is connected with a power source plug through a circuit. The top of the water container has an opening to output humidity. Although the structure of this kind of heaters is simple, its effect is not perfect. Accordingly, the inventor of the present invention has devoted himself based on his many years of practical experiences to solve this problem.

SUMMARY OF THE INVENTION

The primary objective of the present invention is to provide a heater with a humidifying device to overcome the shortcomings of the prior art. Through a cotton rod, water is sent to an atomization plate to directly generate atomized particles. The design and structure of the present invention are simple. The heater is combined with the air purifying device, the humidifying device and the heating device to provide multiple functions. The air outlet is to exhaust warm wind, humidified air and purified air, so the user can feel fresh but not dry warm wind.

In order to achieve the aforesaid objective, the heater of the present invention comprises a casing, a heating device, an air purifying device, a humidifying device, and a touch control panel. The casing has an accommodation room therein. The casing has an air inlet and an air outlet thereon. An air inlet passage, a heating passage, a purifying passage, and air outlet passage are formed in sequence between the air inlet and the air outlet. The heating device is mounted in the accommodation room of the casing. The heating device comprises an exhaust fan and a heating member. The exhaust fan is disposed in the air inlet passage. The exhaust fan has an air suction opening facing the air inlet passage of the casing. The heating member is disposed in the heating passage corresponding to the air supply opening of the exhaust fan. The air purifying device is installed in the purifying passage to purify air flowing through the purifying passage. The humidifying device comprises a water container, a cotton rod, a fixing knob, an atomization plate, a hollow pipe, and a fog output box. The water container has a water inlet. The cotton rod is inserted into the water container from the water inlet to suck water in the water container and send the water to the atomization plate. The fixing knob is rotatably connected to the water inlet of the water container to fix an upper end of the cotton rod. The atomization plate is disposed on top of the fixing knob and in contact with the cotton rod. The atomization plate generates atomized particles to be sent to the hollow pipe. One end of the hollow pipe is connected to the fixing knob through a connector. Another end of the hollow pipe is connected to the fog output box. The atomized particles generated by the atomization plate passes through the hollow pipe to be exhausted through the fog output box. The water container, the cotton rod, the fixing knob, and the atomization plate of the humidifying device are installed in the accommodation room of the casing. The fog output box of the humidifying device is installed at a front side of the casing and corresponds in position to the air outlet. The touch control panel is installed to the casing. The touch control panel is electrically connected with the heating device, the air purifying device, and the humidifying device, respectively.

Compared to the prior art, the present invention has obvious advantages and effects. The atomization plate is connected with the water inlet of the water container to form an integral one. The water is delivered to the atomization plate through the cotton rod to generate atomized particles. The design and structure of the present invention are simple for easy assembly and production. Besides, the heater is combined with the air purifying device, the humidifying device and the heating device to provide multiple functions. The air outlet is to exhaust warm wind, humidified air and purified air, so the user can feel fresh but not dry warm wind.

DETAILED DESCRIPTION OF THE PREFERRED EMBODIMENTS

Embodiments of the present invention will now be described, by way of example only, with reference to the accompanying drawings.

Figure 1:
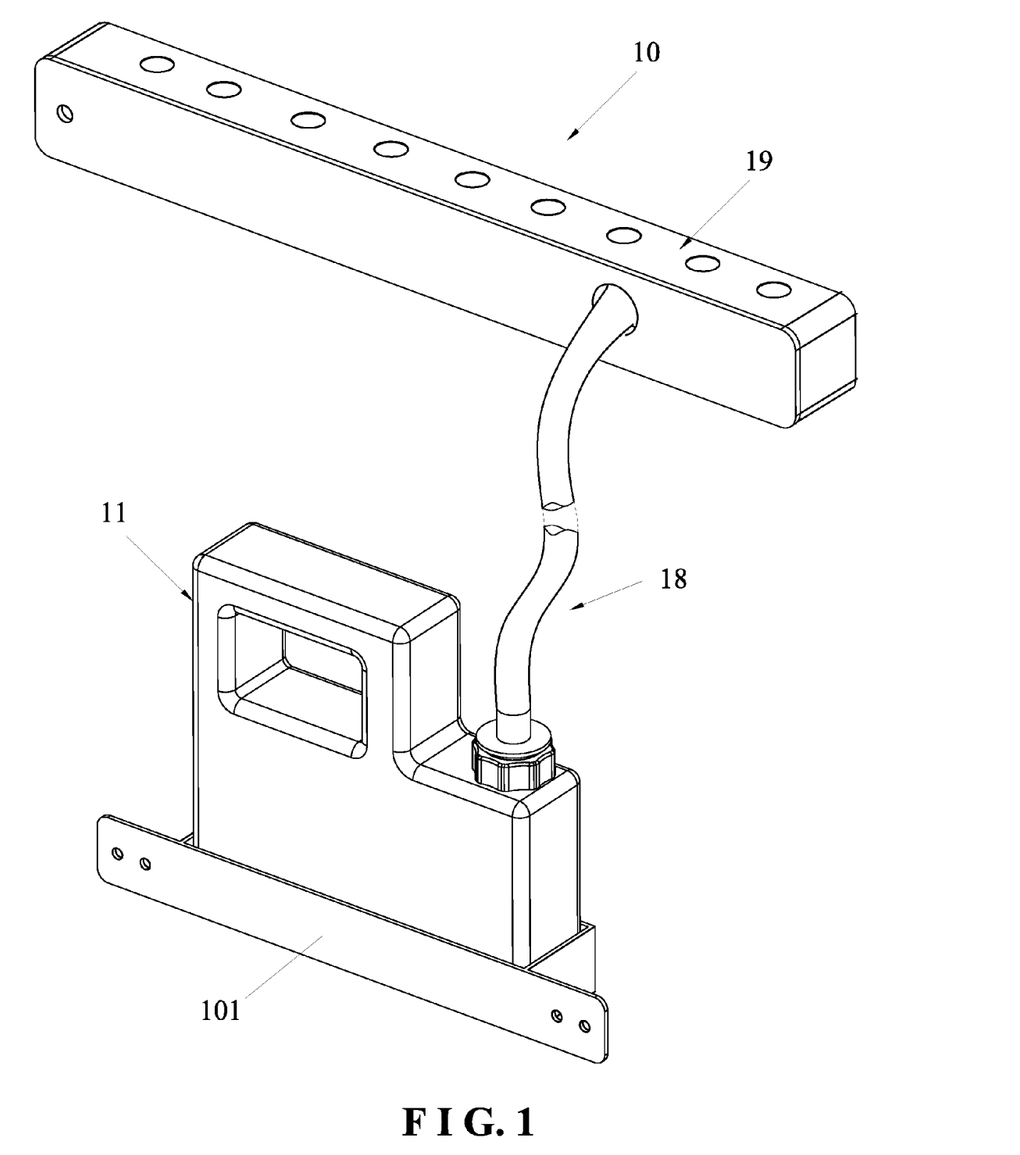
FIG. 1 is a perspective view showing the humidifying device according to a preferred embodiment of the present invention.
Figure 2:
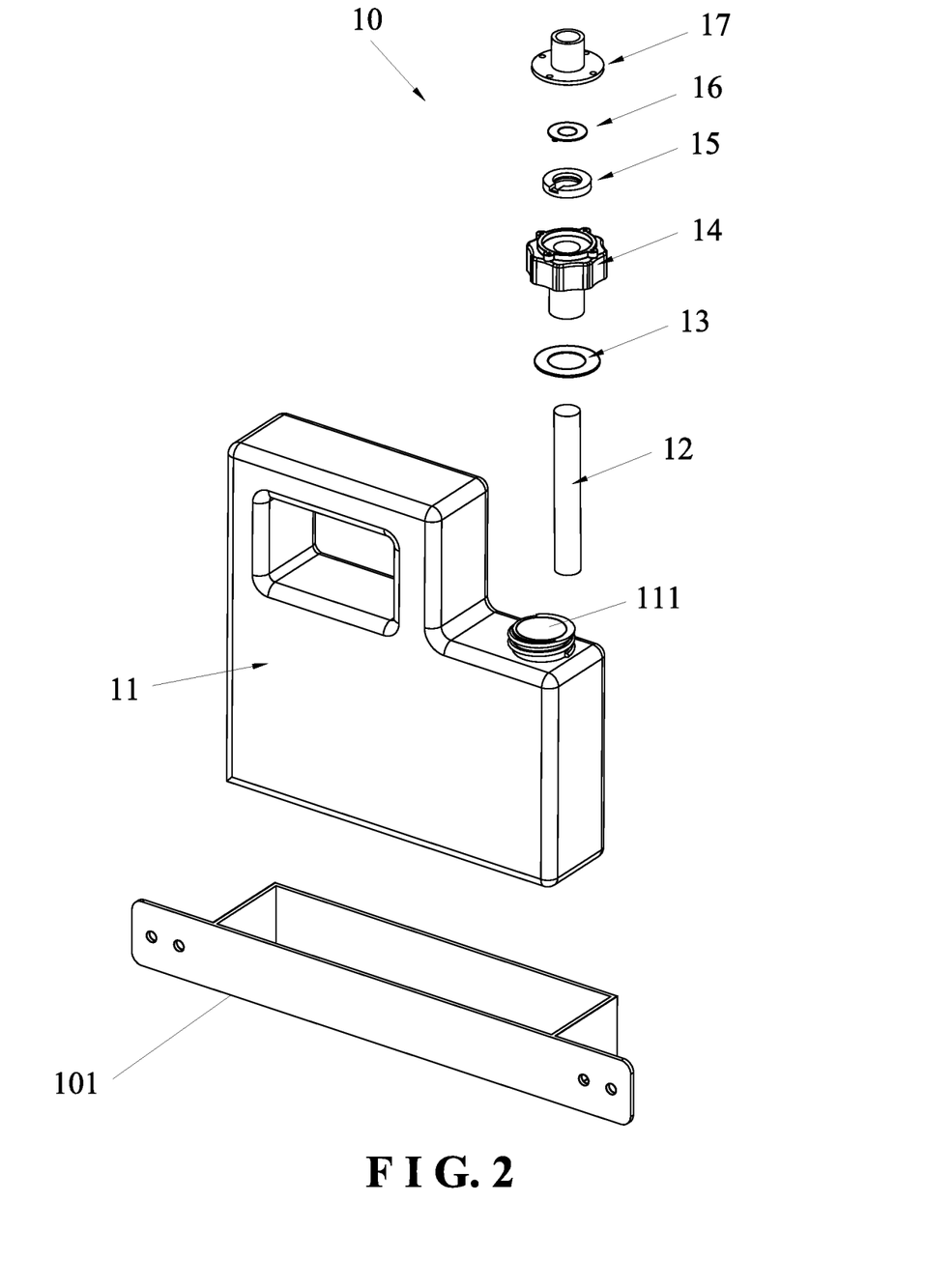
FIG. 2 is an exploded view showing the humidifying device according to the preferred embodiment of the present invention.

FIG. 1 and FIG. 2 show a humidifying device 10 according to a preferred embodiment of the present invention. The humidifying device 10 comprises a water container retainer 101, a water container 11, a cotton rod 12, a waterproof ring 13, a fixing knob 14, a seal gasket 15, an atomization plate 16, a connector 17, a hollow pipe 18, and a fog output box 19.

The water container retainer 101 is adapted to drain water and to retain the water container 11. The water container 11 supplies water to the cotton rod 12. The water container 11 supplies water to the cotton rod 12. The water container 11 has a water inlet 111. The cotton rod 12 is inserted into the water container 11 from the water inlet 111 to suck the water in the water container 11 and send the water to the atomization plate 16. The fixing knob 14 is rotatably connected to the water inlet 111 of the water container 11 to fix the upper end of the cotton rod 12. The waterproof ring 13 is disposed between the fixing knob 14 and the water inlet 111 of the water container 11 to prevent the water container 11 from leaking, providing a sealing function. The atomization plate 16 is disposed on top of the fixing knob 14 and in contact with the cotton rod 12. The atomization plate 16 vibrates to generate atomized particles to be sent to the hollow pipe 18. The seal gasket 15 is disposed between the atomization plate 16 and the fixing knob 14 to prevent leakage after the atomization plate 16 vibrates, providing a sealing and elastic function. One end of the hollow pipe 18 is connected to the fixing knob 14 through the connector 17. The connector 17 is to tighten the atomization plate 16 to prevent it from loosening. Another end of the hollow pipe 18 is connected to the fog output box 19. The atomized particles generated by the atomization plate 16 are sent to the fog output box 19 through the hollow pipe 18 to exhaust humidity.

In the present invention, the atomization plate 16 of the humidifying device 10 is connected with the water inlet 111 of the water container 11 to form an integral one for easy installation. The hollow pipe 18 of the humidifying device 10 can be a soft pipe or a hard pipe for delivering the atomized water to the fog output box 19. The connector 17 between the hollow pipe 18 and the fixing knob 14 can be a fixed connector or a snap-in connector to achieve a quick installation. Furthermore, the fixing knob 14 is provided with a water detection switch. When the water level of the water container 11 is lower than the pre-set value to cause that the cotton rod 12 lacks water, the water detection switch will automatically cut off the power source of the atomization plate 16 to achieve smart monitor and control of the water level.

The humidifying device 10 of the present invention is assembled as the following process. The cotton rod 12 is connected with the water container 11. The atomization plate 16 is secured to on the fixing knob 14. The fixing knob 14 is further connected with the cotton rod 12. The fog output box 19 is connected with the hollow pipe 18.

As shown in FIG. 3 to FIG. 8, a heater 1 is provided with the humidifying device 10. The humidifying device 10 is disposed in the heater 1 for exhausting warm but not dry air. The heater 1 comprises a casing 20, a heating device 30, an air purifying device 40, the humidifying device 10, and a touch control panel 50.

The casing 20 has an accommodation room 21 therein. The casing 20 has an air inlet 22 and an air outlet 23 thereon. The air inlet 22 is disposed at a rear side of the casing 20. The air outlet 23 is disposed at a front side of the casing 20. An air inlet passage 24, a heating passage 25, a purifying passage 26, and air outlet passage 27 are formed in sequence between the air inlet 22 and the air outlet 23. The heating device 30 is mounted in the accommodation room 21 of the casing 20. The heating device 30 comprises an exhaust fan 31 and a heating member 32. The exhaust fan 31 is disposed in the air inlet passage 24. The exhaust fan 31 has an air suction opening facing the air inlet passage 24 of the casing 20. The heating member 32 is disposed in the heating passage 25 corresponding to the air supply opening of the exhaust fan 31. The air purifying device 40 is installed in the purifying passage 26 to purify the air flowing through the purifying passage 26. The water container 11, the cotton rod 12, the fixing knob 14, the atomization plate 16 of the humidifying device 10 are installed in the accommodation room 21 of the casing 20. The fog output box 19 of the humidifying device 10 is installed at the front side of the casing 20 and corresponds in position to the air outlet 23. The touch control panel 50 is installed at the front side of the casing 20. The touch control panel 50 is electrically connected with the heating device 30, the air purifying device 40, and the humidifying device 10 respectively for showing the temperature, humidity and light alarm.

Figure 3:
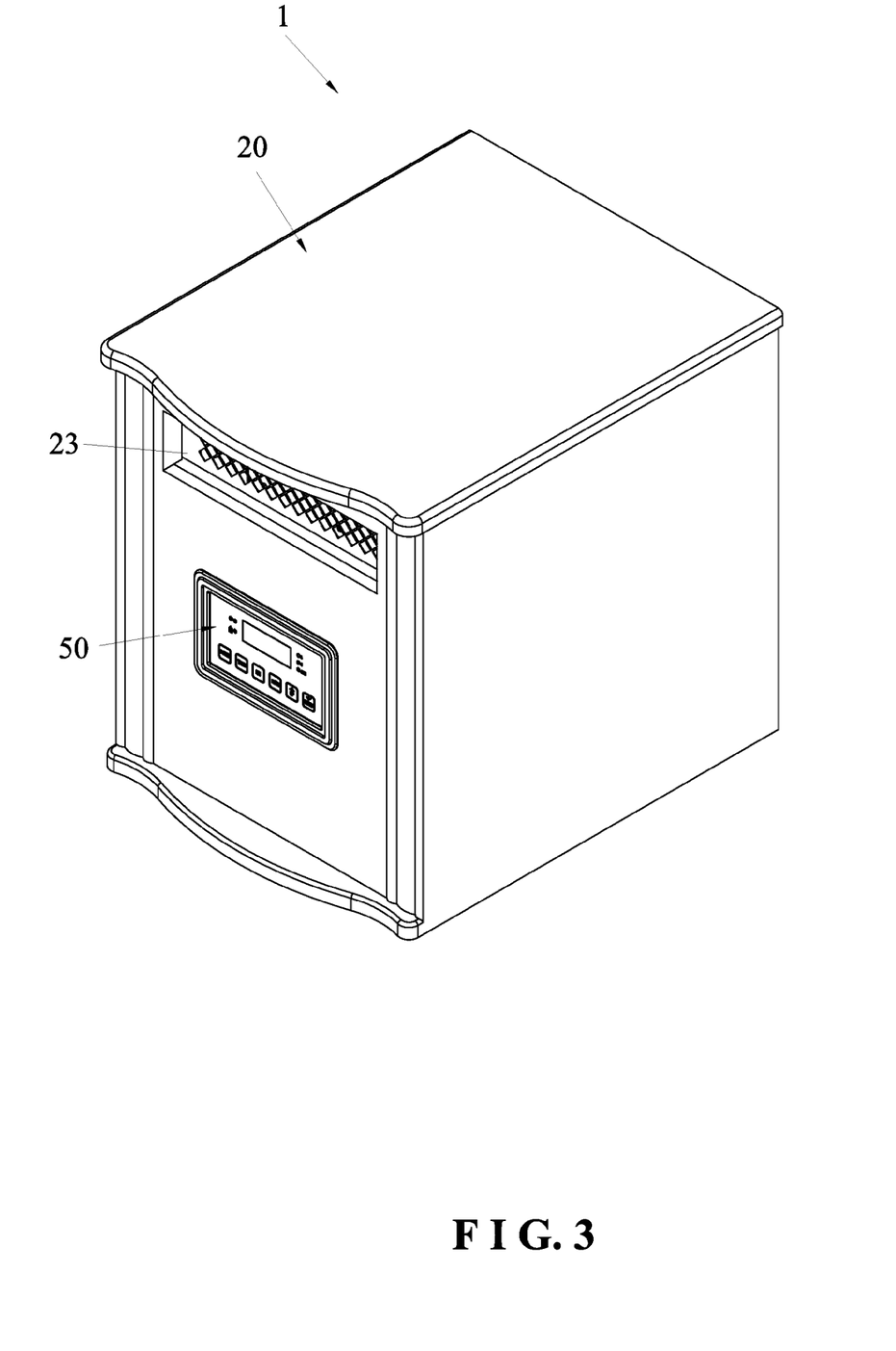
FIG. 3 is a perspective view showing the heater according to the preferred embodiment of the present invention.
Figure 4:
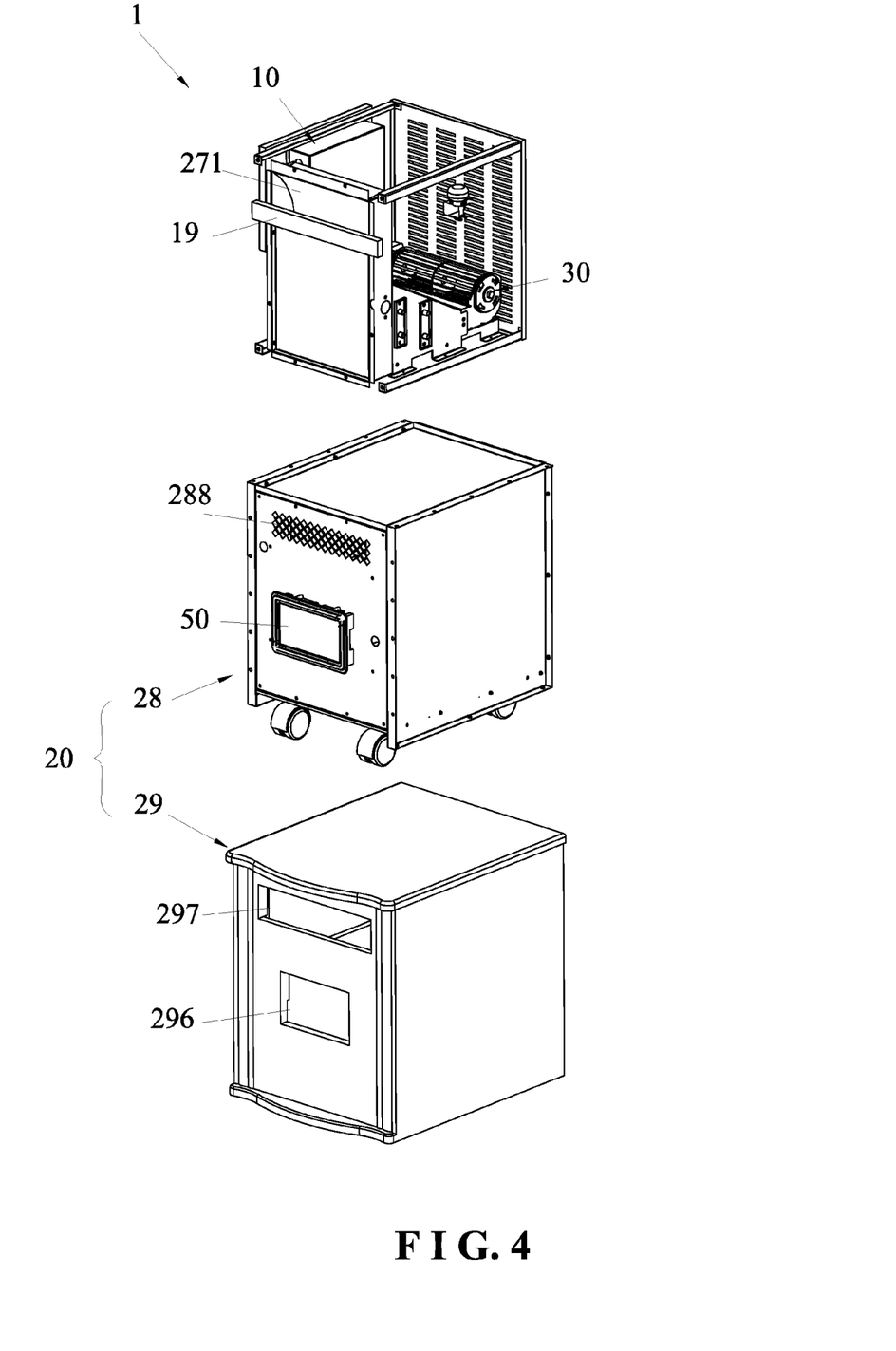
FIG. 4 is a first exploded view showing the heater according to the preferred embodiment of the present invention.
Figure 5:
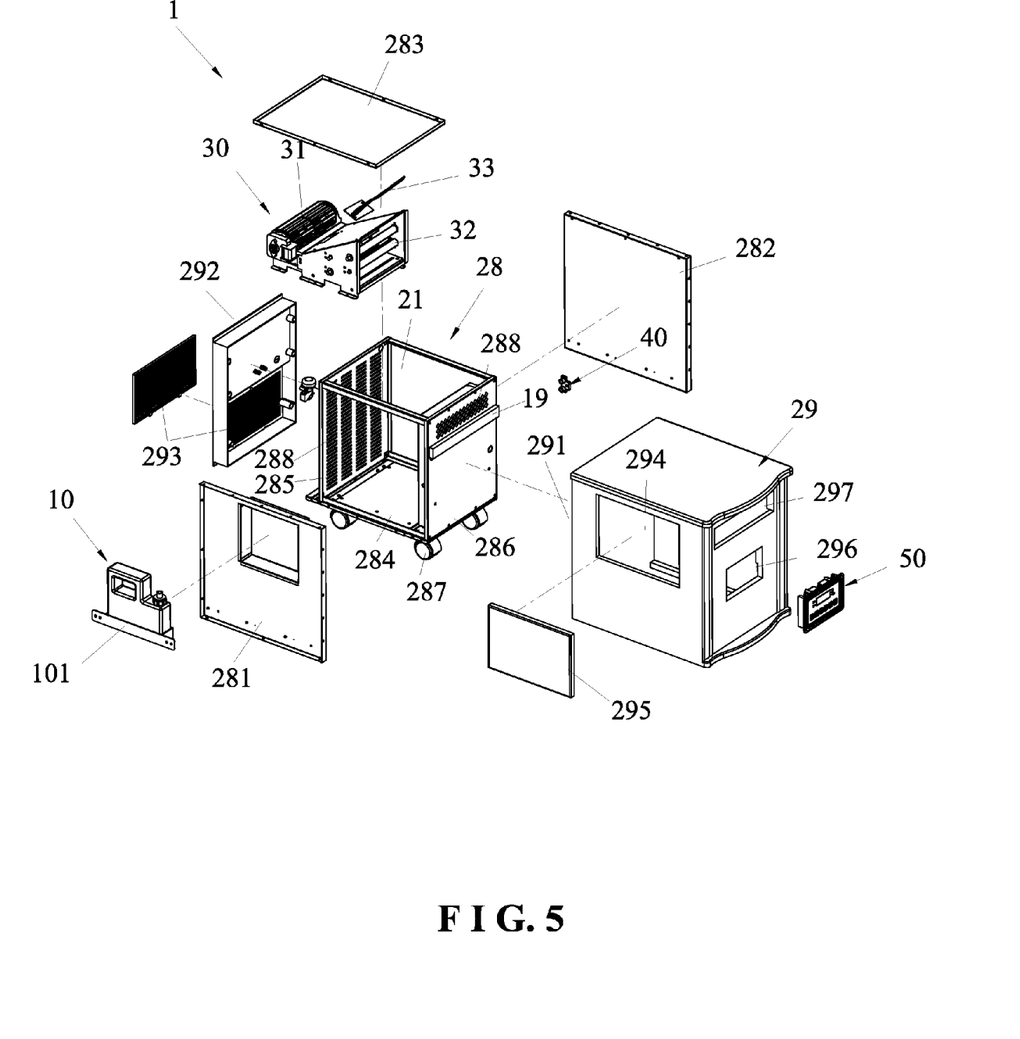
FIG. 5 is a second exploded view showing the heater according to the preferred embodiment of the present invention.

Specifically, as shown in FIG. 3 and FIG. 5, the casing 20 is composed of an inner casing 28 and an outer casing 29. The inner casing 28 is made of a metallic material. The outer casing 29 is made of wood. The outer casing 29 has an opening 291 at the back thereof. The inner casing 28 is placed into the outer casing 29 from the opening 291. After the inner casing 28 is placed into the outer casing 29, a back plate 292 is provided to seal the opening 291. The lower section of the back plate 292 is provided with a dual-layer dustproof filter 293 to block large particles of dust. The left board of the outer casing 29 has a hole 294 for the humidifying device 10 to be installed in the heater 1. After the humidifying device 10 is installed, a decoration board 295 is provided to cover the hole 294 to beautify the appearance of the heater 1. The front of the outer casing 29 is formed with an installation hole 296 and an air vent 297. The installation hole 296 is for the touch control panel 50 to be installed therein, such that the user can operate the heater 1 at the front of the heater 1 and the data displayed by the touch control panel 50 can be read easily.

The inner casing 28 is composed of a left board 281, a right board 282, a top board 283, a bottom board 284, a rear board 285, and a front board 286. The bottom board 284 is provided with rollers 287 for moving conveniently. The rear board 285 is formed with meshes 288 to input air smoothly and to block big particles of dust. The upper section of the front board 286 is also formed with meshes 288 to output air smoothly and to separate the exterior from the interior passages of the heater 1 at the air outlet 23. This prevents the user's fingers from reaching into the exterior of the heater 1 to ensure the safety of use and keeps a beautiful appearance.

Figure 6:
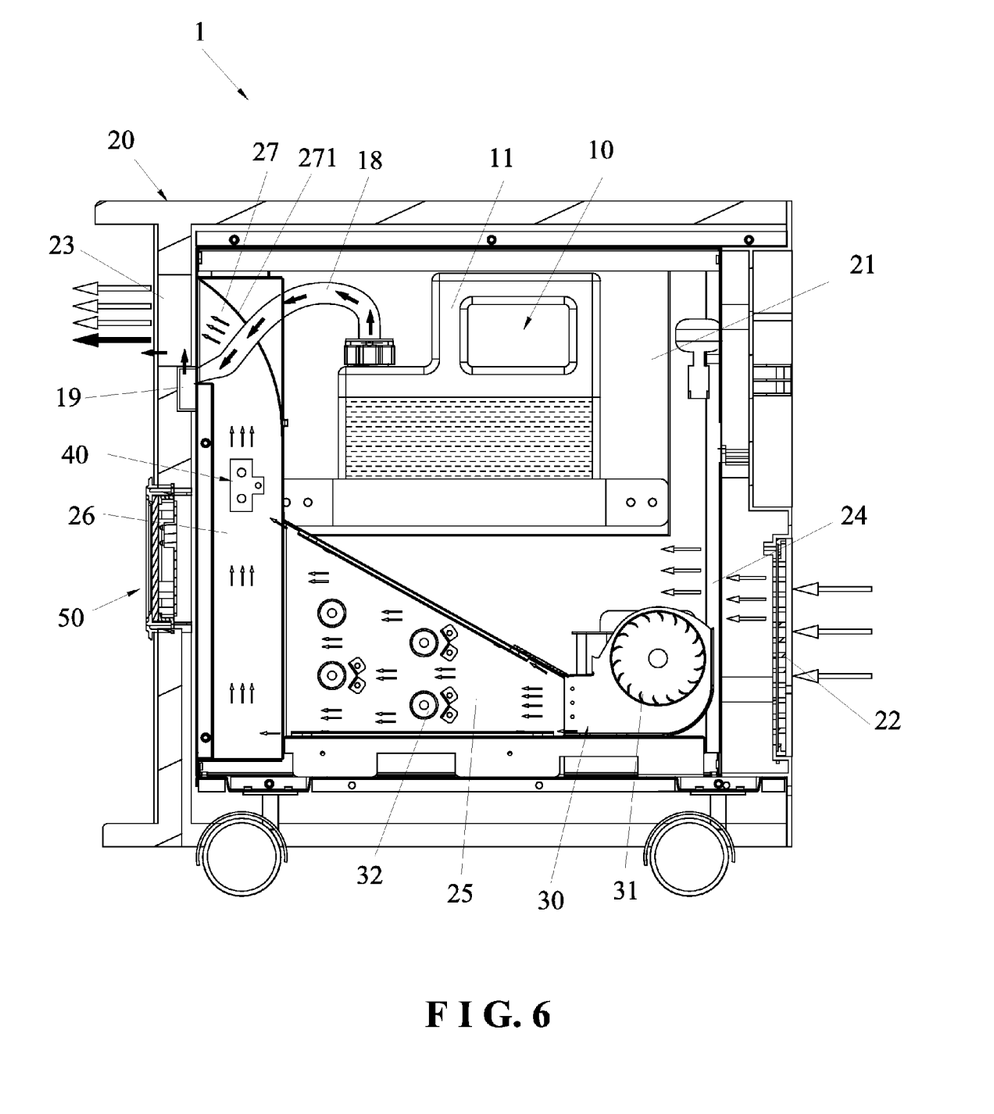
FIG. 6 is a schematic view showing the interior passages of the heater according to the preferred embodiment of the present invention.

As shown in FIG. 6, the air purifying device 40 is a negative ion generator, a positive ion generator, a positive and negative ion generator, or an ozone generator. Because the air purifying device 40 is directly disposed in the purifying passage 26, the wind from the heating device 30 flows through the purifying passage 26 to be purified by the air purifying device 40 to generate negative ions, positive ions, positive and negative ions, or ozone so as to send fresh warm wind out. Furthermore, the air outlet 23 is adapted to exhaust hot wind and purified fresh air. The fog output box 19 of the humidifying device 10 is disposed at the lower end of the air outlet 23. The wind direction of the fog outlet of the fog output box 19 is perpendicular to the wind direction of the air outlet 23 for the humidified and atomized air to be exhausted along with the air of the air outlet 23 to get fresh warm but not dry wind. The air inlet 22 is disposed at the lower section of the rear side of the casing 20. The air inlet passage 24 and the heating passage 25 are disposed at the lower section of the heater 1 in a level direction. The purifying passage 26 is vertically disposed at the front side of the heater 1. The wind direction of the air outlet 23 is parallel to the air inlet 22. A curved wind guide plate 271 is provided at the turning position of the air outlet passage 27 for the air to be blown out smoothly.

In this embodiment, the heating device 30 is provided with a thermo switch 33 for overheating protection. The heating member 32 is a quartz tube heater, a heating coil, or a PTC (positive temperature coefficient) heater. The air suction opening and the air supply opening of the exhaust fan 31 are perpendicular to each other, corresponding to the air inlet passage 24 and the heating passage 25 which are perpendicular to each other. The air suction opening of the exhaust fan 31 faces the air inlet passage 24, and the air supply opening faces the heating passage 25. The exhaust fan 31 is connected between two passages to ensure a strong wind to be blown out.

Figure 7:
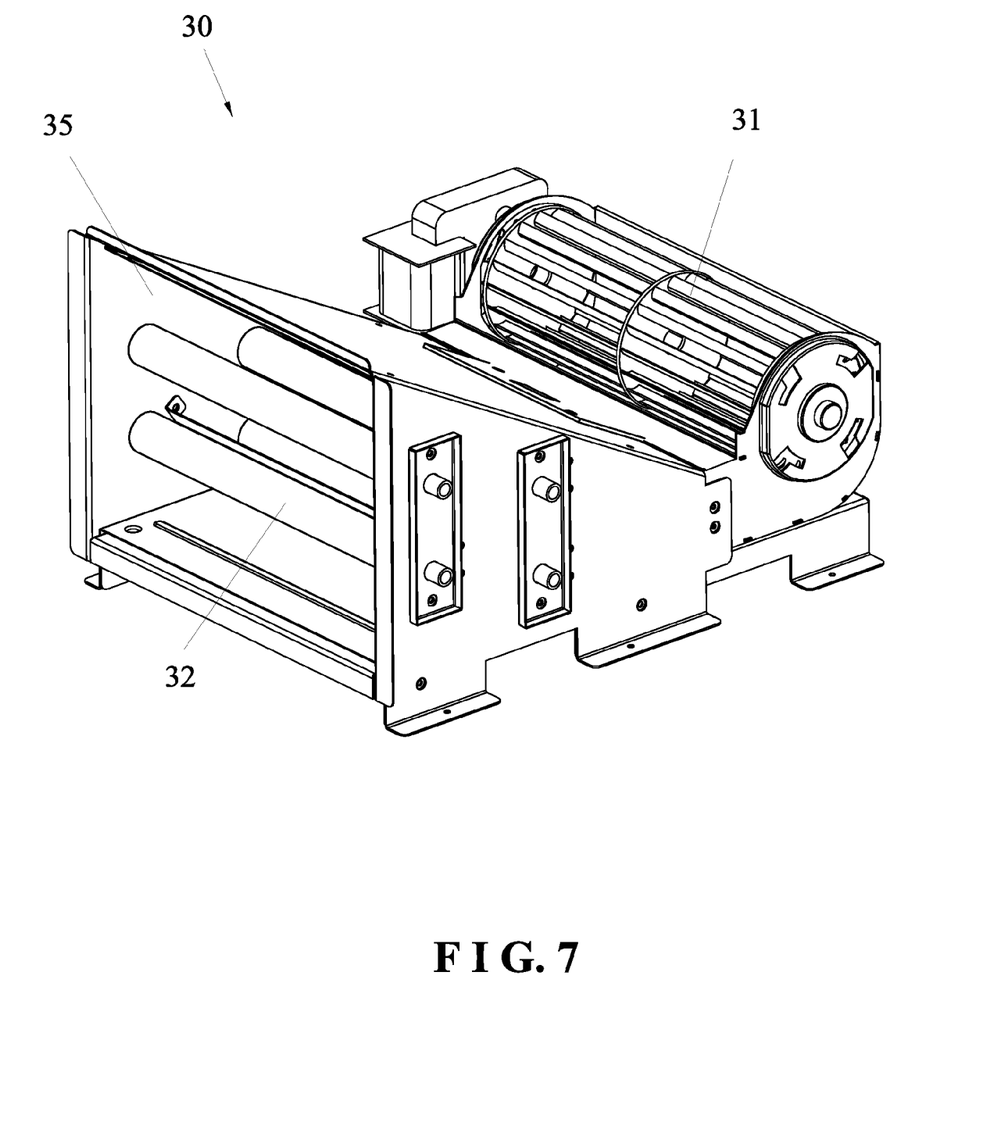
FIG. 7 is a perspective view showing the heating device according to the preferred embodiment of the present invention.
Figure 8:
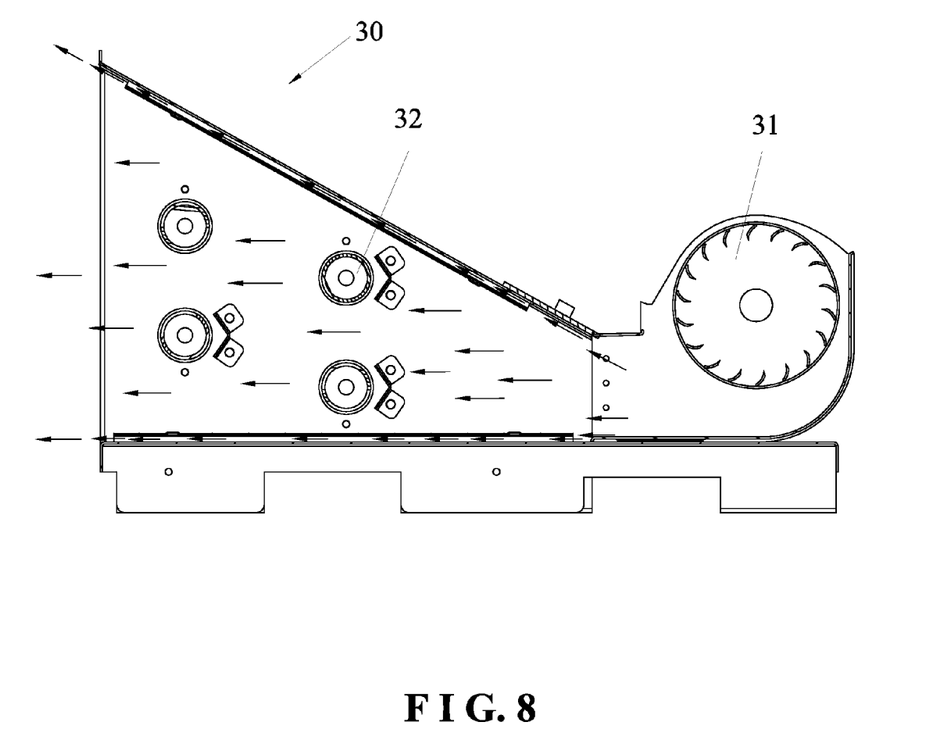
FIG. 8 is a schematic view showing the wind direction of the heating device according to the preferred embodiment of the present invention.

As shown in FIG. 7 and FIG. 8, the heating device 30 is provided with a thermo switch 33 for overheating protection. The heating member 32 is a quartz tube heater, a heating coil, or a PTC (positive temperature coefficient) heater. The lower end of the heating passage 25 is level, and the upper end of the heating passage 25 is enlarged. The heating passage 25 has a level wind guide passage at the inner side of the bottom board 284 and an oblique wind guide passage at the inner side of the top board 283, such that the wind from the exhaust fan 31 can be evenly exhausted along the entire heating passage 25. In addition, the enlarged opening of the heating passage 25 communicates with the purifying passage 26 better to ensure a strong wind to be blown out.

The work principle of the heater 1 is described hereinafter. When the heating device 30 is started, the exhaust fan 31 will inhale the air from the air inlet 22 at the back of the heater 1 and the air inlet passage 24 to enter the exhaust fan 31. Before entering the exhaust fan 31, the outer casing 29 of the heater 1 is provided with multiple filters to filter dust, preventing big particles of dust from damaging the exhaust fan 31. The air supply opening of the exhaust fan 31 is directly connected with the heating passage 25. The heating member 32 in the heating passage 25 heats the air to generate warm wind. The warm wind flows to the purifying passage 26. The air purifying device 40 is disposed in the purifying passage 26 to generate negative ions, positive ions, positive and negative ions, or ozone for the warm wind to be more fresh. The fresh warm wind is guided by the wind guide plate 271 of the air outlet passage 27 and exhausted from the air outlet 23 at the front of the heater 1. The humidifying device 10 can be synchronously started when the heater 1 is started, alternatively, it can be manually started according to the demand of the user. After the humidifying device 10 is started, the atomization plate 16 vibrates to atomize the water in the water container 11. The atomized particles are delivered to the fog output box 19 through the hollow pipe 18. The fog outlet of the fog output box 19 corresponds to the air outlet 23, so that the air outlet 23 is to exhaust the warm wind, humidified air and purified air.

The touch control panel 50 makes the operation of the electric fireplace 1 more convenient. Through the touch control panel 50, the user can turn on/off the heater 1 and starts the heating device 30, the air purifying device 40, and the humidifying device 10 by way of various election modes. Besides, the detection data of the detection switch of each device can be shown on the panel. For example, when the water level of the water container 11 is too low, the water detection switch will automatically cut off the power source of the atomization plate 16. The signal output end of the water detection switch is connected with the signal input end of the touch control panel. The panel will show a light alarm.

The feature of the present invention is that the atomization plate 16 is connected with the water inlet 111 of the water container 11 to form an integral one. The water is delivered to the atomization plate 16 through the cotton rod 12 to generate atomized particles. The design and structure of the present invention are simple for easy assembly and production. Besides, the heater 1 is combined with the air purifying device 40, the humidifying device 10 and the heating device 30 to provide multiple functions. The air outlet 23 is to exhaust warm wind, humidified air and purified air, so the user can feel fresh but not dry warm wind.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A heater with a humidifying device, the heater comprising:
   a casing, the casing having an accommodation room therein, the casing having an air inlet, an air outlet thereon, an air inlet passage, a heating passage, a purifying passage, and air outlet passage;
   the air inlet passage, the heating passage, the purifying passage, and the air outlet passage being formed in sequence between the air inlet and the air outlet;
   wherein the heating passage is shaped as a trapezoid with a lower end of thereof being level and the upper end thereof being enlarged such that the heating passage serves as a level air guide passage above an inner side of a bottom board, but as a oblique air guide passage under another inner side of a top board, with the bottom board and top board parallel to each other,
   the purifying passage is disposed in front of both a humidifying device and a heating passage, and disposed at a front of the heater perpendicularly to the bottom board (284);
   the air inlet passage and the heating passage are disposed at a lower section of the heater in a level direction; and
   a heating device, the heating device being mounted in the accommodation room of the casing, the heating device comprising an exhaust fan and a heating member, the exhaust fan being disposed in the air inlet passage, the exhaust fan having an air suction opening facing the air inlet, the heating member being disposed in the heating passage corresponding to an air supply opening of the exhaust fan;
   an air purifying device, the air purifying device being installed in the purifying passage to purify air flowing through the purifying passage;
   the humidifying device comprising a water container, a cotton rod, a fixing knob, an atomization plate, a hollow pipe, and a fog output box;
   the water container having a water inlet;
   the cotton rod being inserted into the water container from the water inlet to suck water in the water container and send the water to the atomization plate;
   the fixing knob being rotatably connected to the water inlet of the water container to fix an upper end of the cotton rod;
   the atomization plate being disposed on top of the fixing knob and in contact with the cotton rod, the atomization plate generating atomized particles to be sent to the hollow pipe;
   one end of the hollow pipe being connected to the fixing knob through a connector, another end of the hollow pipe being connected to the fog output box, the atomized particles generated by the atomization plate passing through the hollow pipe to be exhausted through the fog output box, the water container, the cotton rod, the fixing knob, and the atomization plate of the humidifying device being installed in the accommodation room of the casing, the fog output box of the humidifying device being installed at a front side of the casing and corresponds in position to the air outlet, wherein an air flow from a fog outlet of the fog output box is perpendicular to another air flow from the air outlet (23); and a touch control panel, the touch control panel being installed to the casing, the touch control panel being electrically connected with the heating device, the air purifying device, and the humidifying device, respectively.

2. The heater with a humidifying device as claimed in claim 1, wherein a waterproof ring is provided between the fixing knob and the water inlet of the water container, and a seal gasket is provided between the atomization plate and the fixing knob.

3. The heater with a humidifying device as claimed in claim 1, wherein the hollow pipe is one of a soft pipe and a hard pipe.

4. The heater with a humidifying device as claimed in claim 1, wherein the fixing knob is provided with a water detection switch, when the water level of the water container is lower than a pre-set value to result in that the cotton rod lacks water, the water detection switch automatically cuts off a power source of the atomization plate.

5. The heater with a humidifying device as claimed in claim 1, wherein the connector between the hollow pipe and the fixing knob is one of a fixed connector and a snap-in connector.

6. The heater with a humidifying device as claimed in claim 1, wherein the casing is composed of an inner casing and an outer casing, the inner casing is made of a metallic material, the outer casing is made of wood, the outer casing has an opening at a back thereof, and the inner casing is placed into the outer casing from the opening.

7. The heater with a humidifying device as claimed in claim 1, wherein the heating device is provided with a thermo switch for overheating protection.

8. The heater with a humidifying device as claimed in claim 1, wherein the heating member is one of a quartz tube heater, a heating coil, and a PTC (positive temperature coefficient) heater.

9. The heater with a humidifying device as claimed in claim 1, wherein the air purifying device is one of a negative ion generator, a positive ion generator, a positive and negative ion generator, and an ozone generator.

* * * * *